(12) United States Patent
Utaka et al.

(10) Patent No.: US 9,448,191 B2
(45) Date of Patent: Sep. 20, 2016

(54) X-RAY FLUORESCENCE SPECTROMETER AND X-RAY FLUORESCENCE ANALYZER

(71) Applicant: Techno-X Co., Ltd., Osaka-shi (JP)

(72) Inventors: Tadashi Utaka, Takatsuki (JP); Koichi Muraoka, Setagaya-ku (JP)

(73) Assignee: Techno-X Co., Ltd., Osaka-shi (JP)

( * ) Notice: Subject to any disclaimer, the term of this patent is extended or adjusted under 35 U.S.C. 154(b) by 370 days.

(21) Appl. No.: 13/725,592

(22) Filed: Dec. 21, 2012

(65) Prior Publication Data

US 2013/0170613 A1 Jul. 4, 2013

(30) Foreign Application Priority Data

Dec. 28, 2011 (JP) ................... 2011-289110

(51) Int. Cl.
*G01N 23/22* (2006.01)
*G01N 23/207* (2006.01)

(52) U.S. Cl.
CPC ...... *G01N 23/2206* (2013.01); *G01N 23/2076* (2013.01)

(58) Field of Classification Search
CPC .................................................. G01N 23/2206
USPC ................................. 378/44–46, 49
See application file for complete search history.

(56) References Cited

U.S. PATENT DOCUMENTS

| | | | | |
|---|---|---|---|---|
| 3,772,522 A * | 11/1973 | Hammond et al. | ............. | 378/84 |
| 4,577,338 A * | 3/1986 | Takahashi et al. | ............. | 378/48 |
| 5,446,777 A * | 8/1995 | Houtman | ........................ | 378/45 |
| 6,023,496 A * | 2/2000 | Kuwabara | ....................... | 378/45 |
| 6,173,037 B1 | 1/2001 | Brouwer | | |
| 6,226,347 B1 * | 5/2001 | Golenhofen | ..................... | 378/45 |
| 6,934,359 B2 | 8/2005 | Chen et al. | | |
| 7,356,114 B2 * | 4/2008 | Kataoka | ................. | G01B 15/02 378/44 |
| 2008/0186477 A1 * | 8/2008 | Wang | ................. | G01N 21/6452 356/73 |
| 2009/0116613 A1 * | 5/2009 | Kataoka et al. | ................ | 378/47 |
| 2011/0194671 A1 | 8/2011 | Chen et al. | | |
| 2014/0072095 A1 * | 3/2014 | Feser | ................. | G01N 23/2206 378/4 |
| 2015/0032398 A1 * | 1/2015 | Peterlinz | ............ | G01N 23/2206 702/81 |

FOREIGN PATENT DOCUMENTS

| | | |
|---|---|---|
| DE | 198 20 861 | 11/1999 |
| DE | 199 31 298 | 2/2000 |
| JP | 03081655 A * | 4/1991 |
| JP | 06-317547 A | 11/1994 |

(Continued)

*Primary Examiner* — Jack Berman
*Assistant Examiner* — James Choi
(74) *Attorney, Agent, or Firm* — W. F. Fasse

(57) ABSTRACT

An X-ray fluorescence spectrometer irradiates a measurement sample 1 with primary X rays from an X-ray source, and excites an element in the sample 1 to emit fluorescence X rays, and the primary X-rays are partially scattered as scattered X rays from the sample 1. A spectroscopic system is placed so that a first spectroscopic unit, a second spectroscopic unit, and a single X-ray detector form an optimized optical system. The first spectroscopic unit disperses the fluorescence X rays to collect the resultant X rays onto the X-ray detector. The second spectroscopic unit disperses the scattered X rays to collect the resultant X rays onto the X-ray detector. In this manner, the spectroscopic system disperses the fluorescence X rays and the scattered X rays so that the intensity of the fluorescence X rays and the intensity of the scattered X rays can be detected by the single X-ray detector 24.

22 Claims, 8 Drawing Sheets

(56) References Cited

FOREIGN PATENT DOCUMENTS

| JP | 07-005127 A | 1/1995 |
| JP | 08-128975 A | 5/1996 |
| JP | H08-201320 A | 8/1996 |
| JP | 2001-091481 A | 4/2001 |
| JP | 2005-140719 A | 6/2005 |

* cited by examiner

CALIBRATION CURVE OF SULFUR IN OIL
BEFORE CORRECTION

CALIBRATION CURVE OF SULFUR IN OIL
AFTER CORRECTION

X-RAY FLUORESCENCE SPECTROMETER AND X-RAY FLUORESCENCE ANALYZER

FIELD

The technology herein relates to X-ray fluorescence spectrometers and X-ray fluorescence analyzers, and more particularly to X-ray fluorescence spectrometers that disperses fluorescence X rays and scattered X rays, and X-ray fluorescence analyzers that perform quantitative analysis by using a spectroscopic system of the X-ray fluorescence spectrometer.

BACKGROUND AND SUMMARY

X-ray fluorescence spectroscopy is divided into energy dispersive X-ray fluorescence analyzers and wavelength dispersive X-ray fluorescence analyzers depending on the dispersion method. The energy dispersive X-ray fluorescence analyzers use a low-power X-ray tube. Thus, the energy dispersive X-ray fluorescence analyzers can be implemented in a desktop configuration and a smaller size. However, the energy dispersive X-ray fluorescence analyzers do not have high analysis accuracy, and thus are not suitable for analysis of trace elements.

The wavelength dispersive X-ray fluorescence analyzers use a high-power X-ray tube. Thus, the wavelength dispersive X-ray fluorescence analyzers have high analysis accuracy, but require liquid nitrogen cooling, which increases the size and cost.

In recent years, as part of efforts to address environmental problems, the standard for trace sulfur ($_{16}S$) as a harmful element contained in oil has been established, and regulation thereof is gradually becoming stricter. Along with this, a test method for ultratrace sulfur analysis is being standardized by the International Organization for Standardization (ISO) and the Japanese Industrial Standards (JIS). Thus, there is a demand for apparatuses capable of analyzing 0.5 ppm level (conventional quantitation limit) or less of sulfur in oil.

In order to satisfy such a demand, X-ray analyzers use a semiconductor detector having a large-area detection element.

However, using a high-power X-ray tube and a large-area X-ray detector requires utilities of large electric power, cooling water, and liquid nitrogen, etc., which increases the apparatus size and significantly increases the apparatus cost. Moreover, the installation area is increased, and a large space is required for installation. Frequent maintenance is also required, and maintenance cost of the apparatus is significantly increased.

It is a primary object of the present disclosure to provide an X-ray fluorescence spectrometer and an X-ray fluorescence analyzer using a spectroscopic system thereof, which can analyze 0.5 ppm level or less of a trace element in a measurement sample with high accuracy at relatively low cost.

It is another object of the present disclosure to provide an X-ray fluorescence spectrometer and an X-ray fluorescence analyzer using a spectroscopic system thereof, which reduces background of an analyzed element to improve the peak/background (P/B) ratio so that a trace element in a measurement sample can be analyzed.

It is still another object of the present disclosure to provide an X-ray fluorescence analyzer capable of analyzing the content based on the intensity ratio between fluorescence X rays and scattered X rays, and thus having further improved accuracy.

An non-limiting example X-ray fluorescence spectrometer (10, 20) according to the present disclosure includes: an X-ray source (21) that emits primary X rays to irradiate a sample to be measured with the primary X rays; a first spectroscopic unit (22) that disperses fluorescence X rays emitted from the sample; a second spectroscopic unit (23) that disperses scattered X rays scattered from the sample; and a single X-ray detector (24) that is positioned so as to be able to receive the fluorescence X rays dispersed by the first spectroscopic unit and the scattered X rays dispersed by the second spectroscopic unit, and that receives the fluorescence X rays and the scattered X rays.

The numerals in parentheses are the reference numerals of the corresponding elements in example embodiments.

According to the present disclosure, an X-ray fluorescence spectrometer can be obtained which is useful for analyzing 0.5 ppm level or less of a trace element in a sample with high efficiency at relatively low cost.

The fluorescence X rays and the scattered X rays emitted from the sample are dispersed and monochromatized into monochromatic beams by the first spectroscopic unit and the second spectroscopic unit, whereby a spectrum having a higher P/B ratio can be obtained. Moreover, the detection lower limit of the trace element in the oil can be 0.5 ppm or less, and analysis time can be significantly reduced.

The first spectroscopic unit may be formed to have a curved surface, and may be positioned so as to be able to collect the fluorescence X rays onto the X-ray detector. The second spectroscopic unit may be formed to have a curved surface, and may be positioned so as to be able to collect the scattered X rays onto the X-ray detector. The first spectroscopic unit, the second spectroscopic unit, and the single X-ray detector are thus selected so as to achieve an optimal optical arrangement. The X-ray detector may detect the collected fluorescence X rays and scattered X rays.

According to this configuration, an X-ray optical system of the spectroscopic units can be optimized, and the fluorescence X rays and the scattered X rays can be simultaneously detected by the single X-ray detector. Thus, detection accuracy of the fluorescence X rays can further be improved. The first spectroscopic unit may be a first analyzing crystal formed to have a curved surface, and is positioned so as to be able to collect the fluorescence X rays onto said X-ray detector and the curved surface is shaped so as to be tangent to a Rowland circle. The second spectroscopic unit may be a second analyzing crystal formed to have a curved surface, and is positioned so as to be able to collect said scattered X rays onto said X-ray detector and the curved surface is shaped so as to be tangent to a Rowland circle. The X-ray detector may be positioned at an intersection of said Rowland circle of said first analyzing crystal and said Rowland circle of said second analyzing crystal. By the structure the first analyzing crystal, the second analyzing crystal and the X-ray detector are arranged optically optimum and the X-ray detector detects the collected fluorescence X rays and scattered X rays.

The first spectroscopic unit may be placed between the sample and the single X-ray detector, and may guide the fluorescence X rays to the X-ray detector along a first path. The second spectroscopic unit may be placed between the sample and the single X-ray detector on a second path different from the first path, and may guide the scattered X rays emitted from the sample to the single X-ray detector along the second path different from the first path.

Preferably, the first spectroscopic unit is a first analyzing crystal, the second spectroscopic unit is a second analyzing crystal, the first analyzing crystal is selected so that a relation between a wavelength of an element to be measured, which is contained in the sample, and lattice spacing of a crystal material satisfies Bragg diffraction conditions, and so that the curved surface is shaped so as to be tangent to a Rowland circle, the second analyzing crystal is selected so that a relation between a wavelength of a target material of the X-ray source and lattice spacing of a crystal material satisfies the Bragg diffraction conditions, and so that the curved surface is shaped so as to be tangent to a Rowland circle, and the X-ray detector is placed at an intersection between the Rowland circle of the first analyzing crystal and the Rowland circle of the second analyzing crystal.

According to this configuration, efficiency of the X-ray detector is enhanced, and the detection accuracy can further be improved. Preferably, the X-ray detector is a semiconductor X-ray detector having energy resolution, and the semiconductor X-ray detector detects the collected fluorescence X rays and scattered X rays separately.

The X-ray source may be placed so as to irradiate a lower surface of the sample with the primary X rays, the first spectroscopic unit, the second spectroscopic unit, and the X-ray detector may be placed below the sample, and the X-ray detector may be a semiconductor X-ray detector.

According to this configuration, a detection error due to air bubbles can be reduced in the case where the sample is a trace element in liquid such as oil or water. Moreover, the use of the semiconductor X-ray detector allows a low output X-ray tube (several tens of watts) to be used, whereby reduction in cost can be implemented as compared to the case where a high output X-ray tube (several kilowatts or more) is used.

The non-limiting example X-ray fluorescence spectrometer may further includes: a third analyzing crystal (28) that is placed between the X-ray source and the sample, and that monochromatizes the primary X rays from the X-ray source to irradiate the sample with the monochromatized primary X rays.

The non-limiting example X-ray fluorescence spectrometer may further include: a first slit (25); and a second slit (26), wherein the first slit may be provided between the sample and the first spectroscopic unit on the first path, and may collect the fluorescence X rays emitted from the sample and guide the collected fluorescence X rays to the first spectroscopic unit, and the second slit may be provided between the sample and the second spectroscopic unit on the second path, and may collect the scattered X rays scattered from the sample and guides the collected scattered X rays to the second spectroscopic unit.

In another aspect of the present disclosure, an X-ray fluorescence analyzer includes: the X-ray fluorescence spectrometer described above; and a computation unit that obtains an intensity ratio between the fluorescence X rays and the scattered X rays detected by the single X-ray detector, and calculates a content of a trace element in the sample based on the obtained intensity ratio and a calibration curve.

In this aspect, an X-ray fluorescence analyzer can be obtained which is capable of analyzing 0.5 ppm level or less of a trace element in a sample with high accuracy at relatively low cost.

In still another aspect of the present disclosure, an X-ray fluorescence analyzer includes: an X-ray source that emits primary X rays to irradiate a sample to be measured with the primary X rays; a first spectroscopic unit that disperses fluorescence X rays emitted from the sample; a second spectroscopic unit that disperses scattered X rays scattered from the sample; a single X-ray detector that is positioned so as to be able to receive the fluorescence X rays dispersed by the first spectroscopic unit and the scattered X rays dispersed by the second spectroscopic unit, and that receives the fluorescence X rays and the scattered X rays; and a computation unit that obtains an intensity ratio between the fluorescence X rays and the scattered X rays detected by the single X-ray detector, and calculates a content of a trace element in the sample based on the obtained intensity ratio and a calibration curve.

Preferably, the computation unit includes a calibration curve table in which a result of obtaining the intensity ratio between the fluorescence X rays and the scattered X rays for every content in each of a plurality of samples having known contents of a trace element is registered in advance, a ratio calculating unit that obtains the intensity ratio between the fluorescence X rays and the scattered X rays of a sample having an unknown content of an element and detected by the X-ray detector, and a content calculating unit that calculates a content of a trace element in the unknown sample by referring to the calibration curve table based on the intensity ratio calculated by the ratio calculating unit.

The X-ray fluorescence analyzer may analyze a content of sulfur in oil.

In a further aspect of the present disclosure, an X-ray fluorescence analysis method includes: a step of placing an X-ray source that emits primary X rays to irradiate a sample to be measured with the primary X rays; a step of placing a first spectroscopic unit that disperses fluorescence X rays emitted from the sample; a step of placing a second spectroscopic unit that disperses scattered X rays scattered from the sample; a step of placing a single X-ray detector that is positioned so as to be able to receive the fluorescence X rays dispersed by the first spectroscopic unit and the scattered X rays dispersed by the second spectroscopic unit, and that receives the fluorescence X rays and the scattered X rays; and a computation step of obtaining an intensity ratio between the fluorescence X rays and the scattered X rays detected by the single X-ray detector, and calculating a content of a trace element in the sample based on the obtained intensity ratio and a calibration curve.

The computation step may include a first step of preparing a calibration curve table in which a result of obtaining the intensity ratio between the fluorescence X rays and the scattered X rays for every content in each of a plurality of samples having known contents of a trace element is registered in advance, a second step of obtaining the intensity ratio between the fluorescence X rays and the scattered X rays of a sample having an unknown content of an element and detected by the X-ray detector, and a third step of calculating a content of a trace element in the unknown sample by referring to the calibration curve table based on the intensity ratio calculated by the second step.

In a still further aspect of the present disclosure, an X-ray fluorescence spectrometer includes: an X-ray source that emits primary X rays; an analyzing crystal that monochromatizes the primary X rays from the X-ray source to irradiate the sample with the monochromatized primary X rays; a first spectroscopic unit that disperses fluorescence X rays emitted from the sample irradiated with the primary X rays monochromatized by the analyzing crystal; a second spectroscopic unit that disperses scattered X rays scattered from the sample; and a single X-ray detector that is positioned so as to be able to receive the fluorescence X rays dispersed by the first spectroscopic unit and the scattered X rays dispersed by the second spectroscopic unit, and that receives the fluorescence X rays and the scattered X rays.

According to this aspect, the background can be reduced. Thus, a peak of the fluorescent X rays can be made to appear, and high detection accuracy can be achieved. That is, using the monochromatized primary X rays as an excitation source can reduce the X-ray intensity of the background generated from the sample as much as possible, whereby a spectrum having a high P/B ratio can be obtained.

Preferably, the X-ray detector is a semiconductor X-ray detector having energy resolution, and the semiconductor X-ray detector detects said collected fluorescence X rays and scattered X rays separately.

According to the present disclosure, an X-ray fluorescence spectrometer and an X-ray fluorescence analyzer using a spectroscopic system thereof can be obtained which are capable of analyzing 0.5 ppm level or less of a trace element in a measurement sample with high accuracy at relatively low cost.

Moreover, an X-ray fluorescence spectrometer and an X-ray fluorescence analyzer using a spectroscopic system thereof can be obtained which reduces background of an analyzed element to improve the peak/background (P/B) ratio so that a trace element in a measurement sample can be analyzed. Furthermore, an X-ray fluorescence analyzer can be obtained which is capable of analyzing the content based on the intensity ratio between fluorescence X rays and scattered X rays, and thus having further improved accuracy

DETAILED DESCRIPTION OF NON-LIMITING EXAMPLE EMBODIMENTS

Example embodiments will be described below with reference to the accompanying drawings.

Example embodiments of an X-ray fluorescence spectrometer will be described in which an element contained in oil and harmful to humans, such as sulfur ($_{16}$S) or chlorine ($_{17}$Cl), is analyzed to determine if the content of sulfur etc. in the refined oil is within a range of a predetermined reference value.

(First Example Embodiment)

Figure 1:
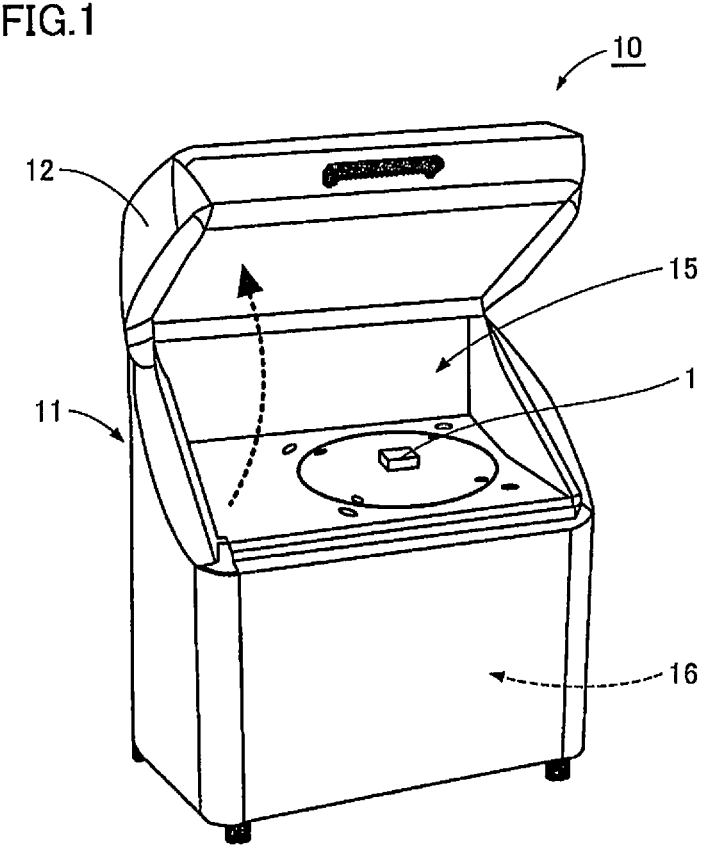
FIG. 1 shows appearance of an X-ray fluorescence spectrometer according to a non-limiting example embodiment.

In FIG. 1, an X-ray fluorescence spectrometer 10 of an example embodiment includes a main body housing 11 and a spectroscopic system 20 (see FIG. 2) accommodated in the main body housing 11. A lid member 12 is provided on the upper part of the main body housing 11 so that the lid member 12 can be opened and closed in the vertical direction. A placing portion (or holding portion) 13 that holds a measurement sample 1 or a sample 1 to be measured (hereinafter sometimes simply referred to as the "sample") is provided in the main body housing 11. The placing portion 13 is exposed when the lid member 12 is opened. Preferably, in order to uniformly irradiate the sample 1 with X rays, part of the placing portion 13 is formed by a rotating table so that the sample 1 is rotatably supported. A window 14 (not shown in FIG. 1; see FIG. 2) is formed in the central part of the placing portion 13 in order to allow the X rays to be radiated therethrough. The placing portion 13 vertically divides the main body housing 11 into an upper measurement chamber 15 and a lower accommodating chamber 16 that accommodates various members of the spectroscopic system 20.

It is more desirable that the inside of the accommodating chamber 16 be replaced with vacuum or helium to about several tens of pascals to suppress attenuation of X rays by air in the optical paths of primary X rays 2 and fluorescence X rays 3.

The main body housing 10 is provided with a lock mechanism (not shown) and a switch (not shown) that detects the open/closed state of the lid member 12, in association with the lid member 12. A shielding member (not shown) such as lead is attached to the wall surface of the accommodating chamber 16 of the main body housing 10. Thus, the main body housing 11 is sealed, and the X rays are prevented from leaking to the outside.

Figure 2:
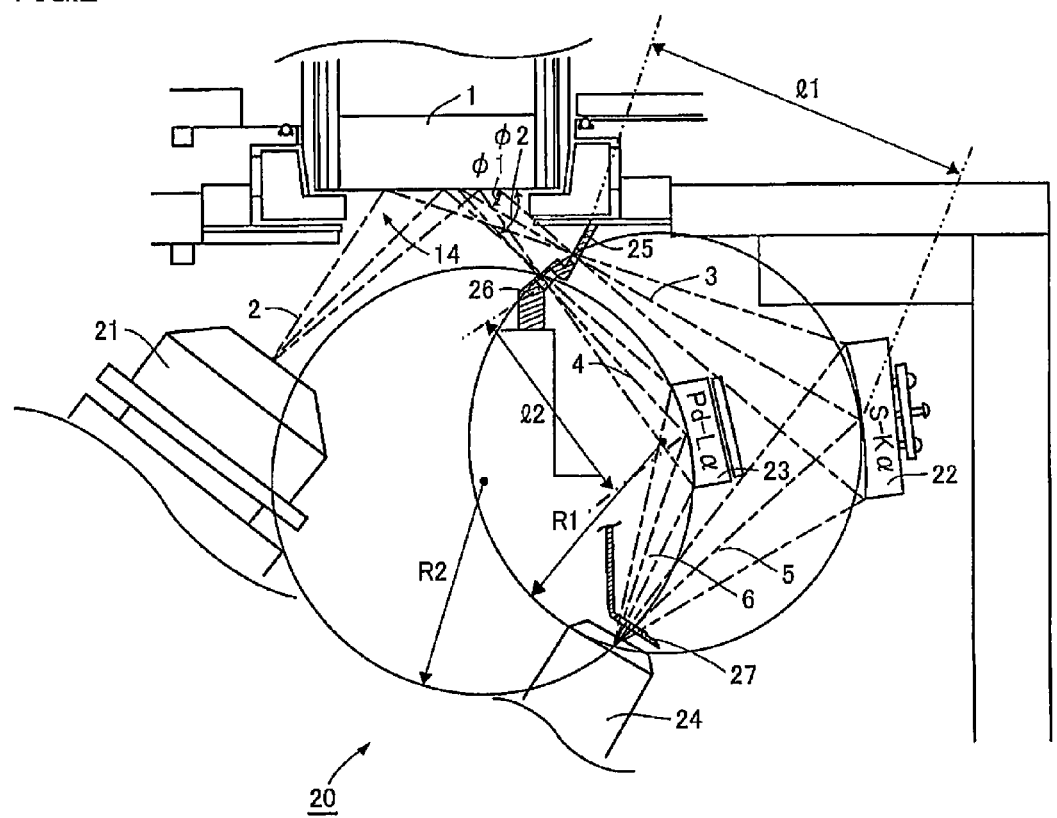
FIG. 2 specifically shows a spectroscopic system of the X-ray fluorescence spectrometer according to the non-limiting example embodiment.

In FIG. 2, the spectroscopic system 20 of the X-ray fluorescence spectrometer 10 is configured so that an X-ray tube 21 as an example of an X-ray source, a first spectroscopic unit 22, a second spectroscopic unit 23, and a single X-ray detector 24 are arranged in an optimal optical arrangement under the sample 1.

Specifically, the X-ray tube 21 is placed on one side (the left side in the figure; also referred to as the "primary side") below the sample 1 so as to face upward (or obliquely upward) so that the X-ray tube 21 directly irradiates the sample 1 with the primary X rays (Pd-Lα rays) at a predetermined angle with respect to the horizontal plane of the lower surface of the sample 1. The angle of the X-ray tube 21 with respect to the horizontal plane of the sample 1 is selected so that the incident angle of the beam center of the primary X ray onto the sample 1 is, e.g., 45 degrees or 90 degrees, in order to achieve the highest intensity of the primary X rays generated by the X-ray tube 21.

An analyzing crystal (or curved monochromator) 22 as an example of the first spectroscopic unit and an analyzing crystal (or curved monochromator) 23 as an example of the second spectroscopic unit are placed on the other side (the right side in the figure; also referred to as the "secondary side") below the sample 1. The analyzing crystal 22 is positioned so that it can receive fluorescence X rays (S—Kα rays) 3 emitted from the sample 1. The analyzing crystal 23 is positioned so that it can receive scattered X rays 4 emitted (or reflected) from the sample 1.

The analyzing crystal 22 has a curved reflective surface, and is placed on an extended line of the beam center of the fluorescence X ray 3 so that the analyzing crystal 22 can collect the fluorescence X rays 3 emitted from the sample 1 at an angle φ1 (i.e., a take-off angle of the fluorescence X rays 3; e.g., φ1=30° to 40°. The analyzing crystal 23 has a curved reflective surface, and is placed on an extended line of the beam center of the scattered X ray 4 so that the analyzing crystal 23 can collect the scattered X rays 4 emitted (or reflected) from the sample 1 at an angle φ2 (i.e., a reflection angle of the scattered X rays 4; e.g., φ2=45°.

The fluorescence X rays 3 emitted at the reflection angle φ1 are collected by the curved surface of the analyzing crystal 22 via a slit 25 provided near the sample 1. The scattered X rays 4 emitted at the reflection angle φ2 are collected by the curved surface of the analyzing crystal 23 via a slit 26 provided near the sample 1.

The conditions for selecting the shapes of the curved surfaces of the analyzing crystals 22, 23 and the distances l1, l2 between the analyzing crystal 22, 23 and the slit 25, 26 will be described later.

The X-ray detector 24 is placed at a position where the fluorescence X rays 3 emitted from the sample 1 are dispersed by the analyzing crystal 22 and collected as monochromatic beams 5 and the scattered X rays 4 are dispersed by the analyzing crystal 23 and collected as monochromatic beams 6 (at the intersection between a Rowland circle with a radius R1 and a Rowland circle with a radius R2, described below).

In other words, the X-ray detector 24 is placed at the intersection between the monochromatic beams 5 collected by the analyzing crystal 22 and the monochromatic beams 6 collected by the analyzing crystal 23.

An anti-scattering plate 27 having a through hole is provided in front of the X-ray detector 24 between the X-ray detector 24 and the analyzing crystals 22, 23. The anti-scattering plate 27 serves to limit incidence of scattered X rays traveling from anywhere other than the analyzing crystals 22, 23 onto the X-ray detector 24.

Figure 3:
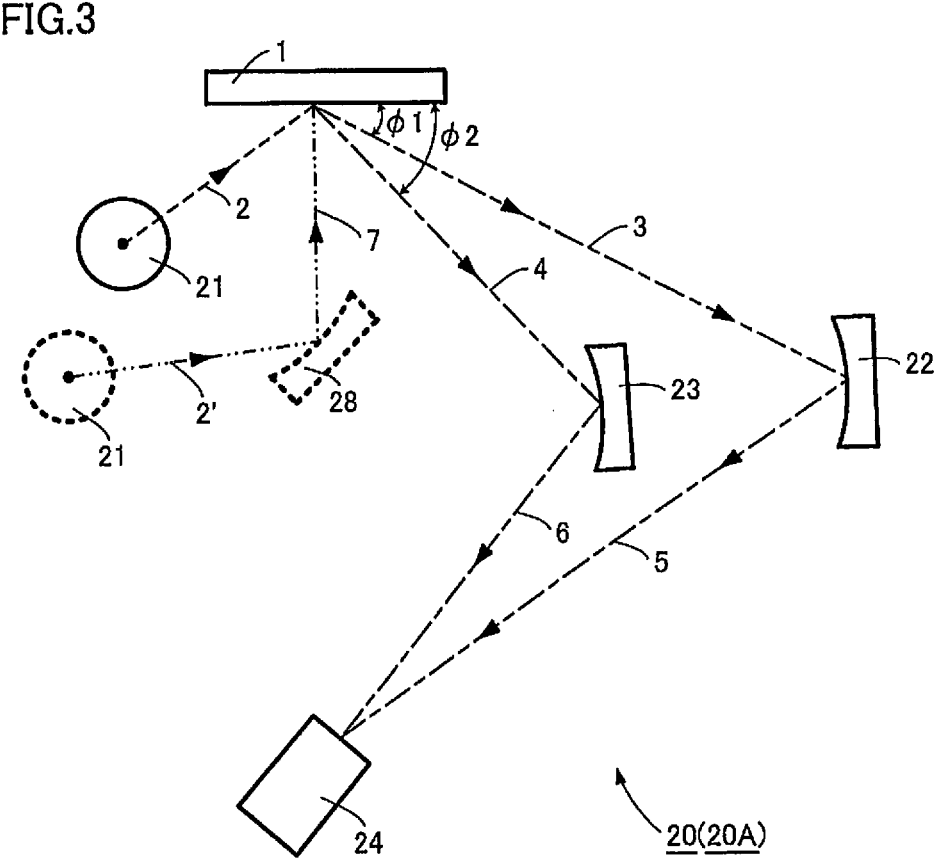
FIG. 3 schematically shows the spectroscopic system.

FIG. 3 schematically shows such an optimal optical arrangement of the spectroscopic system 20.

The optimal optical arrangement of the spectroscopic system 20, the conditions for selecting each portion, etc. will be described in detail below.

The X-ray tube 21 used as an X-ray source preferably has a target made of palladium ($_{46}$Pd) in order to reduce the background, in particular to remove interfering rays. Alternatively, the target may be made of rhodium ($_{45}$Rh), silver ($_{47}$Ag), or chromium ($_{24}$Cr). In the example embodiment, a low-power X-ray tube of several tens of watts is used as the X-ray tube 21.

The window (through hole) 14 is formed in the central part of the placing portion 13 in order to allow the sample 1 to be irradiated with the primary X rays 2 therethrough. A window cover (or filter) mounted in the window (through hole) 14 is desirably made of a film of a polymer (Mylar, Kapton, etc.) having a thickness of several micrometers or a thin film of beryllium ($_4$Be) having a thickness of about 20 μm, in order to reduce absorption of the fluorescence X rays emitted by a trace amount of sulfur as much as possible.

The analyzing crystal 22 has a curved reflective surface, and is positioned on the extended line of the reflection angle φ1 of the fluorescence X rays 3 emitted from the sample 1, so that the analyzing crystal 22 can collect the fluorescence X rays 3. The analyzing crystal 22 is formed to have the curved surface by bending a tabular crystal into a cylindrical shape with a diameter (2·R1) and polishing the resultant crystal so as to form a Rowland circle tangent to the center of the crystal surface (the reflective surface) and having a radius R1.

The analyzing crystal 23 has a curved reflective surface, and is positioned on the extended line of the reflection angle φ2 of the scattered X rays 4 emitted from the sample 1, so that the analyzing crystal 23 can collect the scattered X rays 4. The analyzing crystal 23 is formed to have the curved surface by bending a tabular crystal into a cylindrical shape with a diameter (2·R2) and polishing the resultant crystal so as to form a Rowland circle tangent to the center of the crystal surface (the reflective surface) and having a radius R2.

As described above, in the spectroscopic system of the analyzing crystal 22, the slit 25 is placed on the circumference of the Rowland circle tangent to the curved surface and having the radius R1, and the monochromatic beams 5 of the fluorescence X rays 3 Bragg-reflected by the curved surface are collected on the circumference of the Rowland circle. In the spectroscopic system of the analyzing crystal 23, the slit 26 is placed on the circumference of the Rowland circle tangent to the curved surface and having the radius R2, and the monochromatic beams 6 of the scattered X rays 3 Bragg-reflected by the curved surface are collected on the circumference of the Rowland circle. The X-ray detector 24 is placed at the intersection between the Rowland circle (R1) of the analyzing crystal 22 and the Rowland circle (R2) of the analyzing crystal 23, thereby achieving the spectroscopic system 20 having high energy resolution and high sensitivity.

The conditions for optimizing the spectroscopic system 20 are selected as follows.

The curved surfaces (or curvature surfaces) of the analyzing crystals 22, 23 are selected so that the radius R of the Rowland circle, the incident angle θ onto the analyzing crystal, and the distance l satisfy the following equations (1) and (2) as Bragg diffraction conditions.

$$2d \sin \theta = n\lambda \quad (1)$$

In the equation (1), "d" represents lattice spacing (Bragg angle) of the analyzing crystal, "θ" represents the incident angle (or diffraction angle), "λ" represents the wavelength of fluorescence X rays, and "n" represents the order of reflection.

$$l = 2R \sin \theta \quad (2)$$

Thus, the distances l1, l2 of the analyzing crystals 22, 23 can be given by the following equations (2-1) and (2-2), based on the equation (2).

$$l1 = 2R1 \sin \theta1 \quad (2-1)$$

$$l2 = 2R2 \sin \theta2 \quad (2-2)$$

In the equations (2-1) and (2-2), "R1" represents the radius of the Rowland circle of the analyzing crystal 22, and "R2" represents the radius of the Rowland circle of the analyzing crystal 23.

In the case where the fluorescence X rays having the wavelength λ are incident on the analyzing crystal 22 having the lattice spacing d, interference occurs only when the incident angle θ satisfies the equation (1). In other words, since the wavelength λ correlating with a trace element (sulfur) contained in the sample 1 is known, the incident angle θ (in fact, dispersion angle 2θ) can be calculated based on the equation (1), if the crystal material of the analyzing crystal 22, 23 is determined.

The radius R1, R2 of each Rowland circle is obtained if the distance l1, l2 is obtained by the equation (2-1), (2-2). The incident angle θ is obtained by the equation (1) of the Bragg diffraction conditions. In the equation (1), the lattice spacing d and the order of reflection n are determined by the material of the analyzing crystal.

For example, in the analyzing crystal 22 (S—Kα rays; sulfur), 2d=6.708 Å and Bragg angle=53.215° if graphite crystal is used. In the analyzing crystal 23 (Pd-Lα rays; palladium), 2d=8.76 Å and Bragg angle=29.903° if pentaerythritol (PET) crystal is used.

In addition to graphite, an inorganic crystal such as a single crystal of PET, silicon (Si), or germanium (Ge), or a curved crystal formed by an artificial lattice of a sputtered multilayer thin film (W/Si, W/C, etc.) may be used as the crystal material of the analyzing crystal 22, 23. A monochromator or a curved mirror may be used as a substitute spectroscopic unit for the analyzing crystal 22, 23.

It is preferable that the analyzing crystal 22, 23 have a double-curved configuration (bowl shape) rather than a single-curved configuration, so that the X rays are collected on the X-ray detector 24. If a trace element to be measured in the sample 1 is an element other than sulfur, an optimal crystal material is selected according to the type of the element.

The X-ray detector 24 has energy resolution. It is preferable to use as the X-ray detector 24 an X-ray detector that has high energy resolution and that performs electronic cooling by a Peltier element rather than liquid nitrogen cooling. An example of the X-ray detector 24 is a semiconductor X-ray detector such as a silicon drift detector (SDD) or a Si/PIN detector.

Another example of the X-ray detector 24 is a gas-filled proportional counter or a gas scintillation counter.

As described above, the conditions for optimizing the spectroscopic system 20 are selected, and a Johansson spectrometer as an example of a reflection concentration optical system is formed by using the two analyzing crystals 22, 23, whereby the monochromatic beams 5 of the fluorescence X rays 3 and the monochromatic beams 6 of the scattered X rays 4 are collected at the position of the single X-ray detector 24.

A log spiral spectroscope may be used as another example.

The spectroscopic system 20 of this example embodiment irradiates the lower surface of the sample 1 with X rays (bottom irradiation type). If the sample 1 is liquid such as oil or water, using a top irradiation type spectroscopic system may result in reduction in detection accuracy due to a detection error of fluorescence X rays caused by air bubbles that are formed in the sample 1. It should be understood that the top irradiation type spectroscopic system may be used if the spectroscopic system is optimized to such an extent that the detection error due to air bubbles need not be considered.

Functions of the spectroscopic system 20 of the first example embodiment will be described below with reference to FIGS. 2 and 3.

In response to a supply voltage, the X-ray tube 21 emits primary X rays 2 (Pd-Lα rays) and irradiates the sample 1 with the primary X rays 2. Thus, an element contained in the sample 1 is excited by characteristic X rays contained in the primary X rays 2, and fluorescence X rays 3 are emitted at the specific angle φ1. At the same time, the characteristic X rays strike the sample 1, and scattered X rays 4 are emitted from the sample 1. The fluorescence X rays 3 are dispersed and monochromatized into monochromatic beams 5 by the analyzing crystal 22, and the monochromatic beams 5 are detected by the X-ray detector 24. At the same time, the scattered X rays 4 are dispersed and monochromatized into monochromatic beams 6 by the analyzing crystal 23, and the monochromatic beams 6 are detected by the X-ray detector 24.

A semiconductor detector that is commonly used in energy dispersive X-ray fluorescence analyzers can be used as the X-ray detector 24. Since the semiconductor detector itself has energy resolution, the use of the semiconductor detector allows the respective intensities of the fluorescence X rays 3 and the scattered X rays 4 which are detected simultaneously to be separated and output.

In this manner, quantitative analysis (analysis of the content) of an element to be measured (e.g., sulfur) is performed by using the signal ratio and the signal values obtained from the monochromatic beams 5 of the fluorescence X rays 3 and the monochromatic beams 6 of the scattered X rays 4, which are detected by the X-ray detector 24, and the signal values thereof.

Figure 8:
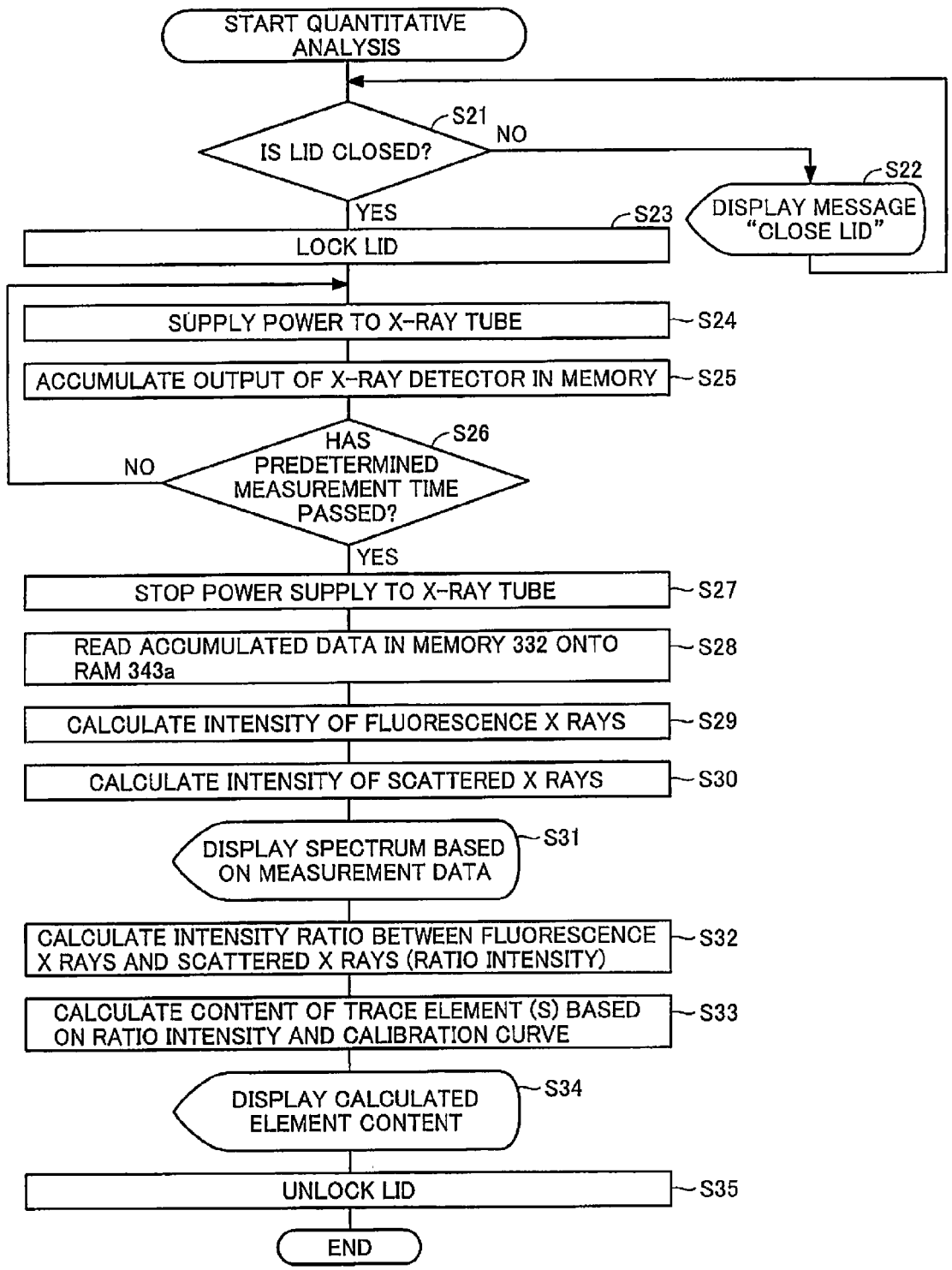
FIG. 8 is a flowchart of analyzing the content of a measurement sample by using the X-ray fluorescence analyzer of the non-limiting example embodiment.

The quantitative analysis of a trace element will be described in detail later with reference to the flowchart of FIG. 8.

(Second Example Embodiment)

Figure 4:
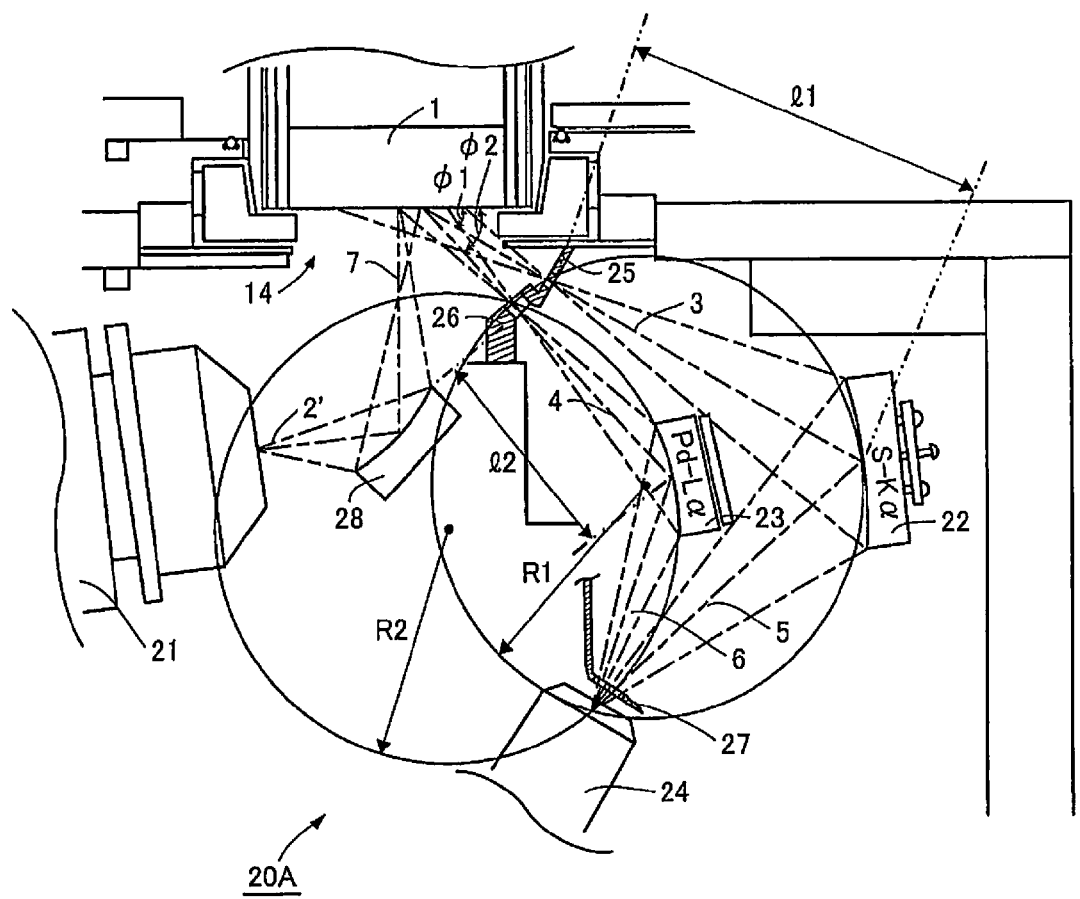
FIG. 4 specifically shows a spectroscopic system of an X-ray fluorescence spectrometer according to another non-limiting example embodiment.

The spectroscopic system 20 of the first example embodiment is described with respect to an example in which the sample 1 is directly irradiated with the primary X rays 2 emitted from the X-ray tube 21. However, a spectroscopic system 20A whose primary side is configured as shown in FIG. 4 may be used.

That is, the primary side may be configured so that an analyzing crystal 28 for monochromatization is placed between the X-ray tube 21 and the sample 1 to monochromatize primary X rays 2' emitted from the X-ray tube 21, and the sample is irradiated with monochromatic beams 7.

In this case, optimal positions and angles of the X-ray tube 21 and the analyzing crystal 28 are selected so that the monochromatic beams 7 resulting from monochromatization and reflection from the analyzing crystal 28 are incident on the sample 1 at a predetermined angle.

Other configurations (the configurations of the parts on the secondary side) are similar to those of the first example embodiment. Like portions are denoted by like reference characters, and description thereof will be omitted. The configurations (21, 28) on the primary side of the spectroscopic system 20A are shown by broken lines in FIG. 3.

In the spectroscopic system 20A of the second example embodiment, the sample 1 is irradiated with the monochromatic rays 7 resulting from monochromatization of the primary X rays 2'. Thus, the spectroscopic system 20A of the second example embodiment is advantageous in that background can further be reduced.

(Third Example Embodiment)

Figure 5:
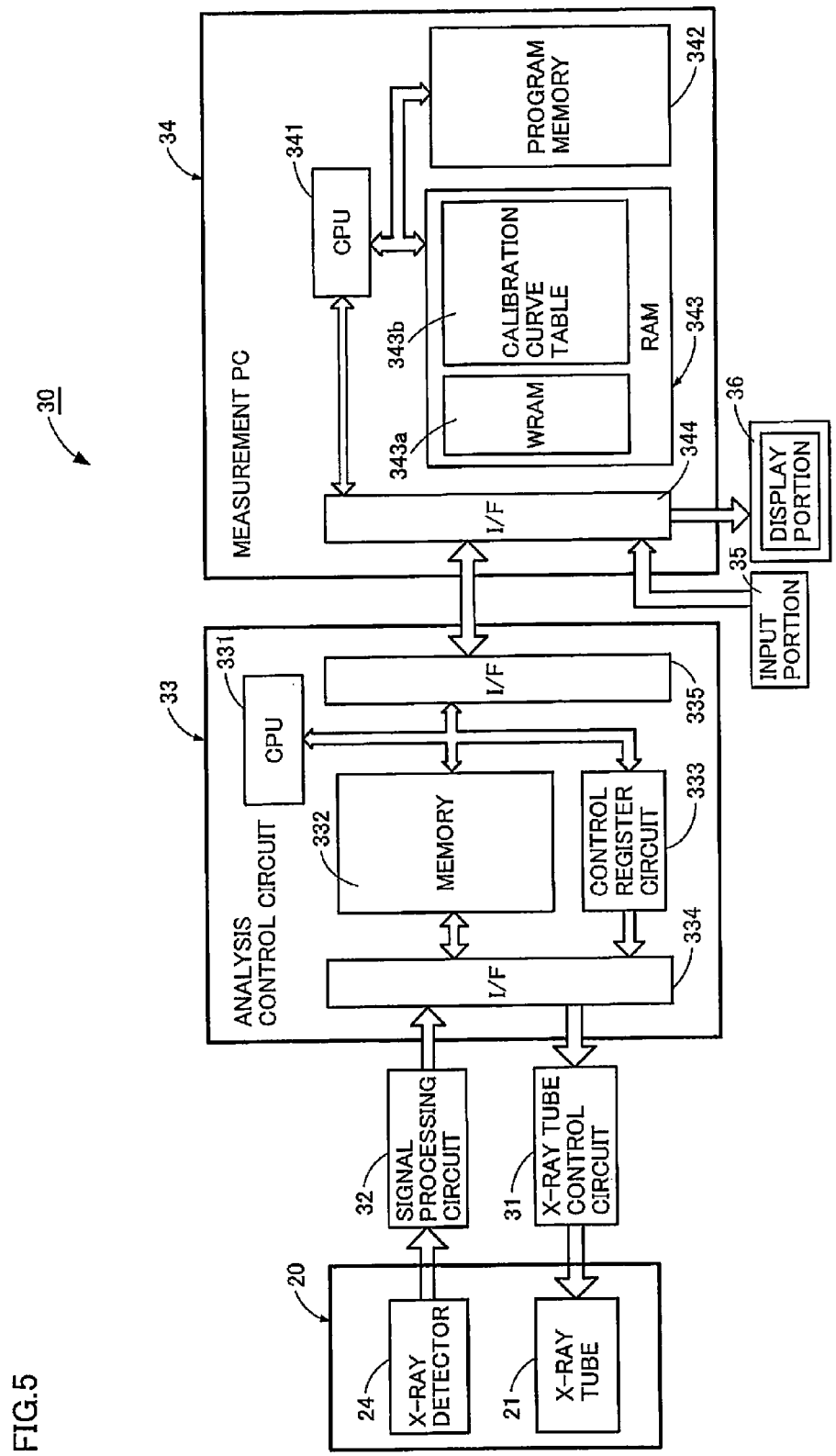
FIG. 5 is a block diagram of an X-ray fluorescence analyzer according to a non-limiting example embodiment.

A detection output of the fluorescence X rays 3 and the scattered X rays 4 from the X-ray detector 24 included in the X-ray fluorescence spectrometer 10 (the spectroscopic system 20) is processed by an X-ray fluorescence analyzer 30 in FIG. 5 to calculate the content of a trace element (e.g., 0.5 ppm or less of sulfur in oil) in the sample 1.

Referring to FIG. 5, the X-ray fluorescence analyzer 30 is connected in association with the X-ray tube 21 and the X-ray detector 24 of the spectroscopic system 20 (or 20A) shown in FIG. 2 or 4. The X-ray fluorescence analyzer 30 in this example embodiment is formed by an X-ray tube control circuit 31, a signal processing circuit 32, an analysis control circuit 33, and a measurement personal computer (PC) 34.

A digital signal processor (DSP) etc. is used as the signal processing circuit 32. The signal processing circuit 32 converts X-ray intensities per unit time (analog values) of the fluorescence X rays 3 and the scattered X rays 4 detected by the X-ray detector 24 into digital values.

The analysis control circuit 33 temporarily stores the digital values obtained by sampling at every unit time in the signal processing circuit 32, and controls the X-ray tube control circuit 31 based on control data from the PC 34 to control electric power to be supplied.

The PC 34 computes the detection data received from the signal processing circuit 32 to measure and analyze the content of an element contained in the sample 1 (sulfur in oil etc.) The PC 34 is used to input measurement conditions, to output necessary information, etc. A general purpose (commercially available) personal computer is used as the PC 34, and a dedicated processing program recorded on a special compact disc read only memory (CD-ROM) or digital versatile disc (DVD) is installed in a program memory 342 of the PC 34 before use.

More specifically, the analysis control circuit 33 includes a central processing unit (CPU) 331, a memory 332 such as a random access memory (RAM), a control register circuit 333, and interfaces 334, 335. The memory 332 cumulatively stores the X-ray intensities of the fluorescence X-rays 3 and the scattered X rays 4 per unit of time detected by the X-ray detector 24, and thus temporarily stores the X-ray intensities during the measurement time.

The control register circuit 333 temporarily stores control information (data of an applied voltage and current) from the PC 34, and outputs the control information to the X-ray tube control circuit 31.

According to the control information, the X-ray tube control circuit 31 controls electric power (applied voltage and current) to be supplied to the X-ray tube 21, and controls the energy of X-rays to be emitted.

The interface 334 controls input/output so as to output an input received from the signal processing circuit 32 to the memory 332 and to output the control data temporarily stored in the control register circuit 333 to the X-ray tube control circuit 31. The interface 335 controls input/output so as to transfer the X-ray intensities (digital values) of the fluorescence X rays and the scattered X rays during the measurement time, which are stored in the memory 332, to the PC 34 and to transfer the control data received from the PC 34 to the control register circuit 333.

The measurement PC 34 includes a CPU 341, the program memory 342, a memory 343 such as a RAM, and an interface 344. A processing program recorded on an external storage medium such as a CD-ROM or DVD is installed in the program memory 342 before the first use of the X-ray fluorescence analyzer 30. The memory 343 has a storage area 343a used as a working RAM ("W-RAM") and a calibration curve table 343b used as a table storage area. In the calibration curve table 343b, the intensity ratio between the fluorescence X rays and the scattered X rays (note that the intensity ratio is also called "ratio intensity" herein) is stored for every known content that is incremented by a unit amount (e.g., 0.1 ppm). Thus, data corresponding to the function of the calibration curve shown in FIG. 6B is registered in the calibration curve table 343b.

An input portion 35 such as a keyboard, a mouse, etc. and a display portion 36 are connected to the interface 344. The interface 344 controls input/output to/from the interface 335, the input portion 35, and the display portion 36.

Known samples of different types (kinds) of oil, namely diesel oil, kerosene, and gasoline, are prepared so that each sample has various sulfur contents incremented by a unit amount. The X-ray intensity of each sample is measured by a conventional large, expensive high-accuracy wavelength dispersive X-ray fluorescence spectrometer. The resultant characteristics of the samples can be represented by three calibration curves shown in FIG. 6A.

Figure 6A:
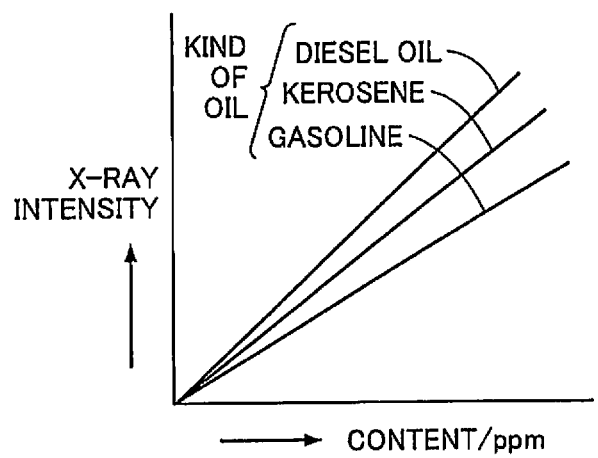
FIG. 6A shows characteristics of different kinds of oil obtained by measuring the intensity of fluorescence X rays of measurement samples having known sulfur contents by using a conventional large high-accuracy wavelength dispersive X-ray fluorescence spectrometer.
Figure 6B:
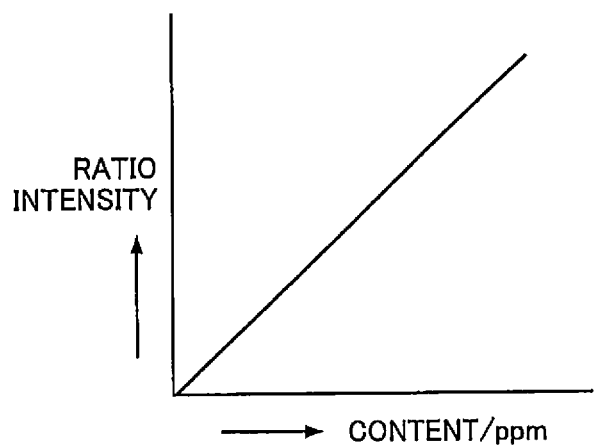
FIG. 6B shows characteristics (calibration curve) obtained by measuring the relation between the sulfur content and the ratio intensity of a known sample by a correction method removing the influence of the kind of sample by using the non-limiting example X-ray fluorescence device of the present disclosure.

FIG. 6A shows that the characteristics of the samples of the same kind of oil having different contents are represented by a linear function. Namely, the intensity of the fluorescence X rays increases linearly. The slope of the line varies depending on the kind of oil. In other words, even if the content is the same, the X-ray intensity and the calibration curve varies depending on the kind of oil. This means that the calibration curve table needs to be registered for each kind of oil.

However, registering the calibration curve table for each kind of oil increases the volume of data, and increases the cost. Moreover, erroneous input (or designation) of the kind of oil causes a detection error because the analyzed sulfur content is regarded as a value for a different kind of oil.

As a solution, this example embodiment uses a correction method that removes the influence of the kind of samples, so that only one calibration curve can be used regardless of the kind of oil.

FIG. 6B is a diagram showing characteristics represented by one calibration curve by using the correction method that removes the influence of the kind of samples. Specifically, a plurality of known samples each having various contents incremented by a predetermined amount (e.g., by 0.1 ppm in a range near a quantitation limit, and by several to several tens of parts per million in a range significantly larger than the quantitation limit) are prepared. The intensity ratio between the fluorescence X rays and the scattered X rays (note that the intensity ratio is also called "ratio intensity" herein) is obtained for each sample by using the X-ray fluorescence analyzer 30 of the example embodiment. The sulfur content is represented on the abscissa, and the intensity ratio or ratio intensity for each content is represented on the ordinate, whereby one calibration curve that is not affected by the kind of oil is obtained.

The intensity of the fluorescence X rays and the intensity of the scattered X rays vary depending on the kind of the sample. However, in this correction method, the intensity ratio or ratio intensity is obtained which varies in proportion to the content regardless of the kind of oil. Thus, characteristics can be represented by a linear function (a function having a constant slope regardless of the kind of oil).

Although the intensity of the scattered X rays is constant regardless of the trace sulfur content in the oil, the intensity of the fluorescence X rays varies in proportion to the trace sulfur content. Thus, obtaining the ratio intensity allows the correlation between the trace sulfur content and the ratio intensity to be represented by one calibration curve.

Accordingly, even if a trace sulfur content is detected and a peak waveform of the X-ray intensity thereof slightly protrudes from the background or is too small to be easily distinguished from the background, the trace content can be detected with high accuracy because the intensity ratio between the fluorescence X rays and the scattered X rays (ratio intensity) is obtained and the content is calculated based on the obtained ratio intensity and the calibration curve.

Figure 7:
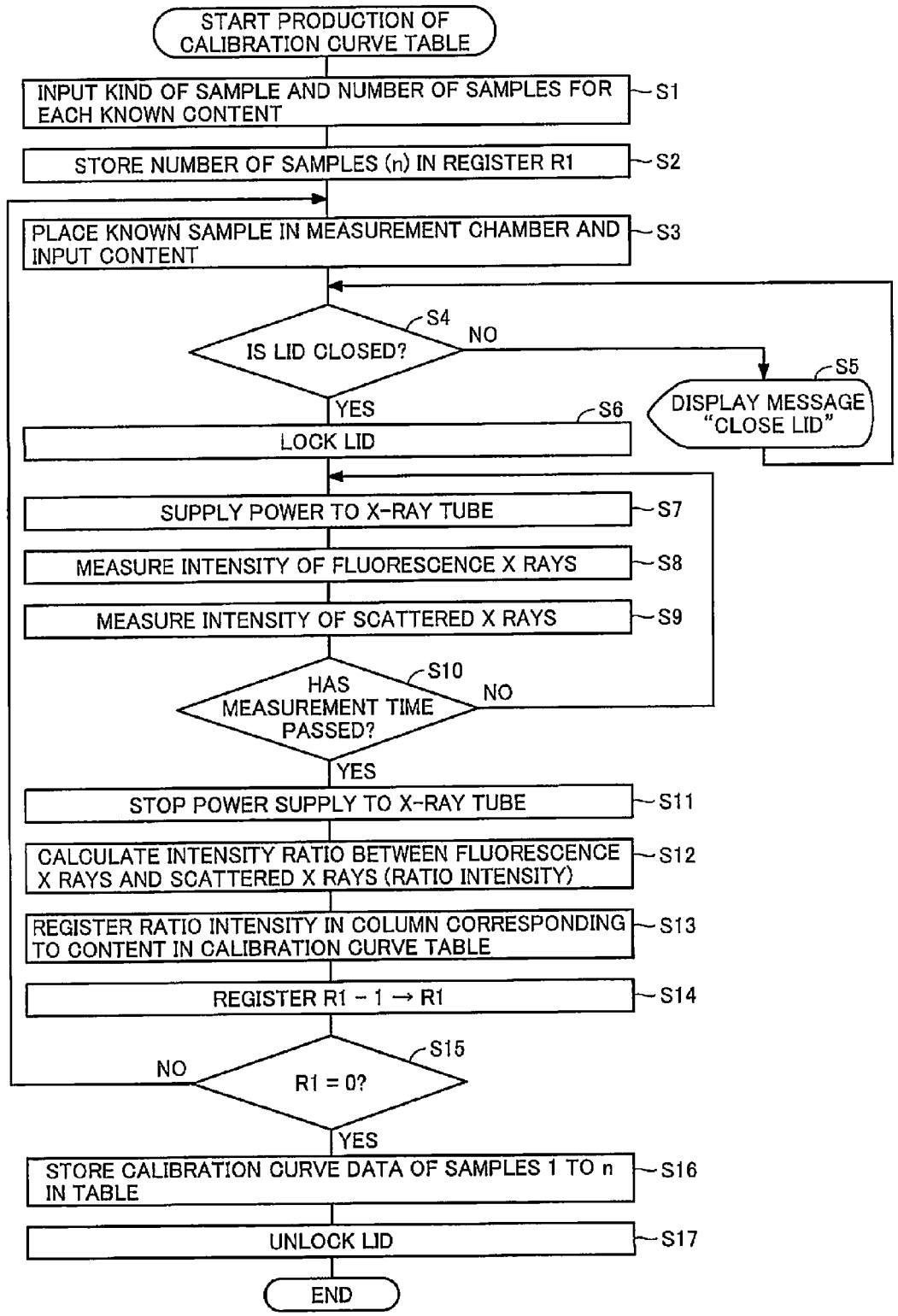
FIG. 7 is a flowchart of producing a calibration curve table by using the X-ray fluorescence analyzer of the non-limiting example embodiment.

Operation of obtaining the calibration curves of FIG. 6A by using the X-ray fluorescence analyzer 30 of FIG. 5 will be described below with reference to the flowchart of FIG. 7.

A plurality of known samples 1 having various contents incremented by a unit amount (e.g., 0.1 ppm) are prepared before calculation of the calibration curve and production of the calibration curve table.

The operator operates the input portion 35 such as a keyboard to input a command to start production of the calibration curve. Thus, the CPU 341 starts the processing of the flowchart of FIG. 7 based on the program stored in the memory 342 of the CPU 341.

In step S1, a message prompting the operator to input the kind of sample and the number of samples (n) for each known content is displayed on the display portion 36. If the operator inputs the kind of sample and the number of samples (n) in response to the message, the input data (the kind of sample and the number of samples) is stored at a certain address included in the W-RAM 343a (e.g., the sample number n is stored in a number-of-sample register R1) in step S2.

In step S3, a sample holder (not shown) containing a first sample 1 having a known content (oil containing a trace amount of sulfur) is placed on the placing portion 13 of the measurement chamber 15, and the lid member 12 is closed. The input portion 35 is operated to input the content in the first sample 1 (e.g., 0.1 ppm). Thus, the content in the first sample 1 is written to the first address of a calibration curve data temporary storage area (an area where data in the stage prior to collectively setting and registering the data of all the samples 1 in the calibration curve table 343b) of the W-RAM 343a.

In step S4, it is determined if the lid member 12 is closed. When lid member 12 is not closed, a message prompting the operator to close the lid member 12 is displayed on the display portion 36 in step S5. If it is determined in step S4 that the lid member 12 is closed, the lid member 12 is locked in step S6.

In step S7, electric power is supplied to the X-ray tube 21. Specifically, data of applied voltage and current values for the X-ray tube 21 is read from the CPU 21, and is temporarily stored in the control register circuit 333. The X-ray tube control circuit 31 controls the applied voltage and current (as a result, electric power) to be supplied to the X-ray tube 21, based on the data of applied voltage and current values.

The X-ray tube 21 is thus excited to emit primary X rays (Pd-L$\alpha$ rays) 2 to irradiate the sample 1 with the primary X rays 2. Fluorescence X rays 3 (S—K$\alpha$ rays) having a wavelength specific to the kind of element (sulfur) contained in the sample 1 are excited from the sample 1. The fluorescence X rays 3 are dispersed by the analyzing crystal 22, and the resultant monochromatic beams 5 are received by the X-ray detector 24.

At the same time, the primary X rays 2 are reflected by the sample 1, and scattered X rays 4 are emitted from the sample 1. The scattered X rays 4 are dispersed by the analyzing crystal 22, and the resultant monochromatic beams 6 are received by the X-ray detector 24. The scattered X rays 4 are independent of the content of the trace element (sulfur) contained in the sample 1, and is dependent on the target material (palladium) of the X-ray tube 21. Thus, the scattered X rays 4 are characteristic X rays of the "Pd-L$\alpha$ rays."

In step S8, the intensity of the fluorescence X rays of the first sample 1 is measured. The intensity of the fluorescence X rays is repeatedly measured at predetermined short time intervals, and the accumulated value of the measurement results is stored in a predetermined area of the memory 332. In step S9, the intensity of the scattered X rays of the first sample 1 is measured. The intensity of the scattered X rays is repeatedly measured at predetermined short time intervals, and the accumulated value of the measurement results is stored in a predetermined area of the memory 332.

In step S10, it is determined if predetermined measuring time has passed. If the measuring time has not passed, the program returns to step S7, and measurement of the intensity of the fluorescence X rays in step S8 and measurement of the intensity of the scattered X rays in step S9 are repeated.

If it is determined in step S10 that the predetermined measuring time (e.g., 5 minutes) has passed, power supply to the X-ray tube 21 is stopped in step S11.

Thus, the accumulated value of the intensity of the fluorescence X rays and the accumulated value of the intensity of the scattered X rays are stored in the corresponding areas of the memory 332.

In the following step S12, the ratio between the accumulated value of the intensity of the fluorescence X rays and the accumulated value of the intensity of the scattered X rays (intensity ratio or ratio intensity) is calculated. In step S13, the calculated ratio between the intensity (accumulated value) of the fluorescence X rays and the intensity (accumulated value) of the scattered X rays (intensity ratio or ratio intensity) of the first sample 1 is written to a predetermined address of the W-RAM 343a which corresponds to the content that is input in step S3.

In this manner, the ratio intensity of the first sample 1 together with the known content is written to the corresponding addresses of the W-RAM 343a.

In step S14, a numerical value "1" is subtracted from the value of the number-of-sample register R1 (initially "n"), and the number of remaining samples to be measured (n−1) is stored in the register R1.

Then, in step S15, it is determined if the value of the number-of-sample register R1 is "0." Step S15 is performed in order to determine if the ratio intensity has been calculated for all of the samples (n samples) that are input in step S1. If the value of the number-of-sample register R1 is not "0," the program returns to step S3.

In step S3, a second sample 1 is placed on the placing portion 13 of the measurement chamber 15, and the input portion 35 is operated to input the content in the sample 1 (e.g., 0.2 ppm). Steps S4 to S15 described above are repeated, and the content in the second sample 1 and its corresponding ratio intensity are written to corresponding addresses of the W-RAM 343a.

Similarly, the ratio intensity of each of third to nth samples 1 is sequentially calculated, and the content in each of the third to nth samples 1 and its ratio intensity are written to corresponding addresses of the W-RAM 343a.

As a result, the contents in the first to nth samples 1 and their calculated ratio intensities are sequentially written to the corresponding addresses of the W-RAM 343a.

The range in which quantitative analysis can be performed is, e.g., 0 ppm to 400 ppm.

If it is determined in step S15 that the value of the number-of-sample register R1 is "0," the program proceeds to step S16. In step S16, the data of the respective measured ratio intensities of the samples (first to nth samples) having the known contents, which is temporarily stored in the W-RAM 343a, is transferred to the calibration curve table 343b, and is stored therein as calibration curve data. Thus, data of the contents of the first to nth samples, which are incremented by a predetermined amount, and their respective ratio intensities are set and registered in the calibration curve table 343b.

In step S16, even if the first to nth samples 1 are not measured in ascending order (or descending order) of the content of the trace element, the contents in these samples 1 may be sorted in ascending order (or descending order) before registration in the calibration curve table 343b, in order to register the data in the calibration curve table 343b in ascending order (or descending order) of the content.

Then, the lid member 12 is unlocked in step S17, and the series of processes is terminated.

The above process of producing the calibration curve table is described with respect to an example in which the ratio intensity corresponding to each content is calculated for a certain kind of oil, and the respective calculated ratio intensities corresponding to the contents are registered in the calibration curve table. Steps S1 to S17 described above are performed in order to produce a calibration curve table of a different kind of samples.

In this case, the intensity ratio between the fluorescence X rays and the scattered X rays is calculated for each of known different contents, and the resultant intensity ratios are registered as ratio intensities. Accordingly, characteristics can be represented by one calibration curve even if the kind of oil is different. Thus, the same result can be obtained as that obtained by registering the ratio intensities calculated by the correction method that removes the influence of the kind of samples.

The above process of producing the calibration curve table need not be performed for every X-ray fluorescence analyzer 30 to be sold. That is, the data of the calibration curve table produced beforehand by the manufacturer and the program data are written to CD-ROMs or DVDs, and new X-ray fluorescence analyzers 30 (or X-ray fluorescence analyzers 30 except the PCs 34) are shipped with the CD-ROMs etc., so that the X-ray fluorescence analyzers 30 are sold together with the CD-ROMs etc.

Before the first use of the X-ray fluorescence analyzer 30, the user (operator) installs the program data and the data of the calibration curve table on a user's personal computer (measurement PC 34). Then, the user performs measurement or analysis. The installed data of the calibration curve table is set and registered in the calibration curve table 343b of the RAM 343, and is referred to when performing analysis of an unknown content of a sample 1 described below.

A process of measuring a sample 1 having an unknown content and analyzing the content will be described below with reference to the flowchart of FIG. 8.

First, the operator places a sample 1 to be measured in a sample holder, and places the sample holder on the placing portion 13. The operator closes the lid member 12, and then depresses a measurement start button or switch. In response to this, the CPU 341 starts the process of the flowchart of FIG. 8, based on the program stored in the memory 342.

In step S21, it is determined if the lid member 12 is closed. If the lid member 12 is not closed (in the opened state), a message prompting the operator to close the lid member 12 is displayed on the display portion 36, and the program waits for the lid member 12 to be closed. If it is detected that the lid member 12 is closed, the lid member 11 is locked in step S23. This inhibits the lid member 12 from being opened during measurement, and prevents leakage of X rays.

In step S24, electric power is supplied to the X-ray tube 21, and primary X rays 2 are emitted from the X-ray tube 21. Since detailed operation is similar to that in step S7, description thereof will be omitted.

In the case of the X-ray fluorescence spectrometer 20, the sample 1 is directly irradiated with the primary X rays (Pd-Lα rays) 2. In the case of the X-ray fluorescence spectrometer 20A, the sample 1 is irradiated with monochromatic beams 7 of the primary X rays 2' via the analyzing crystal 28. Fluorescence X rays 3 having a wavelength specific to the kind of element (sulfur) contained in the sample 1 are excited (emitted) from the sample 1. The fluorescence X rays 3 are dispersed by the analyzing crystal 22, and are received as monochromatic beams 5 by the X-ray detector 24. At the same time, the primary X rays 2 (or the monochromatic beams 7) are reflected by the sample 1, and thereby scattered X rays 4 are emitted from the sample 1. The scattered X rays 4 are dispersed by the analyzing crystal 23, and are received as monochromatic beams 6 by the X-ray detector 24.

In step S25, the X-ray detector 24 detects the fluorescence X rays 3 and the scattered X rays 4, and outputs the detection result as analog values. The analog values of the fluorescence X rays 3 and the scattered X rays 4 are converted to digital values by the signal processing circuit 32, and the digital values are written in the memory 332 and cumulatively stored therein.

In step S26, it is determined if predetermined measurement time (e.g., 5 minutes) has passed. If the predetermined measurement time has not passed, steps S24 to S26 are repeated until the predetermined measurement time passes.

In this manner, the analog values of the intensities of the fluorescence X rays 3 and the scattered X rays 4 detected at relatively short time intervals (sampling cycles) are converted to digital values, and the digital values are cumulatively stored in the memory 332 during the measurement time. If it is determined in step S26 that the predetermined measurement time has passed, power supply to the X-ray tube 21 is stopped in step 527.

In step S28, accumulated data (accumulated value) of the intensity of the fluorescence X rays and accumulated data (accumulated value) of the intensity of the scattered X rays, detected during the measurement time and temporarily stored in the memory 332, are transferred to the W-RAM 343a via the interfaces 335, 334.

In step S29, the intensity of the fluorescence X rays is calculated (or determined) based on the accumulated value of the fluorescence X-ray intensity temporarily stored in the W-RAM 343a. In step S30, the intensity of the scattered X rays is calculated (or determined) based on the accumulated value of the scattered X-ray intensity temporarily stored in the W-RAM 343a.

In step S31, a spectrum is produced based on the intensity (accumulated value) of the fluorescence X rays and the intensity (accumulated value) of the scattered X rays which are stored in the W-RAM 343a, and is displayed on the display portion 36.

The spectrum of the energy (keV) representing the intensity of the scattered X-rays is dependent on the target material (Pd) of the X-ray tube 21, and is combined with the background. Thus, this spectrum has a very large mountain-shaped peak waveform (a mountain shape with gentle slopes) near the wavelength of palladium.

On the other hand, in the case where a trace amount of sulfur near the quantitation limit (0.5 ppm) is contained in the oil, the spectrum of the energy (keV) of the fluorescence X rays has a small mountain-shaped peak waveform that slightly projects from the background near the wavelength specific to the element (sulfur), or a peak waveform that is too small to be easily distinguished from the background.

The intensity of the fluorescence X rays of the trace amount of sulfur is very low as described above. Accordingly, this intensity of the fluorescence X rays cannot be detected by merely removing the background component near the wavelength of sulfur from the energy intensity of the fluorescence X rays, or detection accuracy is very low even if it can be detected.

Therefore, steps S32 and S33 described below are performed.

In step S32, the intensity ratio between the fluorescence X rays and the scattered X rays (ratio intensity) is calculated. By obtaining the ratio between the fluorescence X-ray intensity of sulfur combined (or synthesized) with the background and the scattered X-ray intensity combined with the background, the trace sulfur content can be accurately calculated even if the fluorescence X-ray intensity of sulfur is too low to be easily distinguished from the background.

In step S33, the trace sulfur content is calculated based on the ratio intensity and the calibration curve. That is, by referring to the calibration curve table 343a based on the calculated ratio intensity, the content corresponding to the ratio intensity having the same value, which is registered in advance in the calibration curve table 343b, is read as the calculation result.

In step S34, the calculated sulfur content is displayed on the display portion 36. Then, in step S35, the lid member 12 is unlocked, and the series of processes is terminated.

According to the X-ray fluorescence analyzer 30 of the third example embodiment, even the content of an element (light element) such as a trace amount of sulfur (0.5 ppm or less) is calculated by obtaining the ratio between the fluorescence X-ray intensity and the scattered X-ray intensity calculated (measured) from a sample 1 having an unknown content, and referring, based on the obtained ratio, to the calibration curve table in which the ratio intensities corresponding to the known contents have been registered. Accordingly, the content of the element can be detected with high accuracy even if the amount of element is too small that its peak waveform cannot be easily distinguished from the background.

The first and second example embodiments are described with respect to an example in which the two analyzing crystals (or spectroscopic units) 22, 23 are provided on the secondary side. However, three or more spectroscopic units may be provided on the secondary side.

For example, in order to measure the content of chlorine in addition to sulfur as trace elements in the oil, the position, curved surface, distance, crystal material, etc. of a third analyzing crystal (or spectroscopic unit) are selected in view of the optimization conditions described above. Fluorescence X rays (S—Kα rays) of sulfur are dispersed by the first analyzing crystal 22, fluorescence X rays (Cl—Kα rays) of chlorine are dispersed by the third analyzing crystal, and monochromatic beams dispersed and collected by these analyzing crystals are detected by the single X-ray detector 24.

In this case, calibration curve data of chlorine is calculated in advance and registered as table data in the calibration curve table 343b of the PC 34, as in the case of the calibration curve obtained as the relation between the trace content of sulfur and the ratio intensity as described with reference to the flowchart of FIG. 7.

The above example embodiments are described with respect to an example in which oil is used as an example of the liquid containing a trace element. However, it should be understood that the technical idea of the above example embodiments is also applicable to measurement and/or analysis of a trace content of a harmful element in other liquids such as, e.g., river water, industrial waste, or a plating solution.

The X-ray fluorescence spectrometer 10 and the X-ray fluorescence analyzer 30 of the above example embodiments are useful for measuring and analyzing a trace amount of sulfur, chlorine, etc. contained in oil, and have very high industrial applicability.

The invention claimed is:

1. A combination comprising a test sample to be analyzed and an apparatus for measuring a trace element contained in the test sample, said apparatus comprising:
an X-ray source having a target that emits primary X rays to irradiate the test sample;
a first spectroscopic unit having a first curved surface that is constructed, configured and arranged to selectively receive and disperse fluorescence X rays of the trace element that are emitted from the test sample;
a second spectroscopic unit having a second curved surface that is constructed, configured and arranged to selectively receive and disperse scattered X rays that are scattered from the test sample, wherein the scattered X rays are dependent on said target of said X-ray source and are not dependent on the trace element contained in the test sample;
a single X-ray detector that is positioned so as to receive the fluorescence X rays dispersed by said first spectroscopic unit and to receive the scattered X rays dispersed by said second spectroscopic unit, and that is configured and adapted to detect the fluorescence X rays and the scattered X rays; and
a computation unit that is arranged to receive detection data from said single X-ray detector, and that is configured and adapted to determine, from the detection data, an intensity ratio between a first intensity of the fluorescence X rays and a second intensity of the scattered X rays detected by said single X-ray detector, and to determine a content of the trace element contained in the test sample based on the intensity ratio and a calibration curve;
wherein the trace element contained in the test sample is a light element, and wherein said X-ray source, said single X-ray detector, said first spectroscopic unit and said second spectroscopic unit are respectively selected, configured and arranged so that said apparatus is able to determine the content of the trace element being a light element contained in the test sample.

2. The combination according to claim 1, wherein
said first curved surface of said first spectroscopic unit is positioned and configured so as to collect the fluorescence X rays onto said X-ray detector,
said second curved surface of said second spectroscopic unit is positioned and configured so as to collect the scattered X rays onto said X-ray detector,
said first spectroscopic unit, said second spectroscopic unit, and said single X-ray detector are selected so as to achieve an optimal optical arrangement, and
said X-ray detector is configured and adapted to detect the collected fluorescence X rays and the collected scattered X rays.

3. The combination according to claim 1, wherein
said first spectroscopic unit comprises a first analyzing crystal formed to have said first curved surface, and is positioned so as to collect the fluorescence X rays onto said X-ray detector, and said first curved surface is shaped so as to be tangent to a first Rowland circle,
said second spectroscopic unit comprises a second analyzing crystal formed to have said second curved surface, and is positioned so as to collect the scattered X rays onto said X-ray detector, and said second curved surface is shaped so as to be tangent to a second Rowland circle, said X-ray detector is positioned at an intersection of said first Rowland circle and said second Rowland circle, whereby said first analyzing crystal, said second analyzing crystal and said X-ray detector are arranged optically optimum, and said X-ray detector is configured and adapted to detect the collected fluorescence X rays and the collected scattered X rays.

4. The combination according to claim 1, wherein said first spectroscopic unit is placed between the test sample and said single X-ray detector, and is arranged and configured to guide the fluorescence X rays from the test sample to said X-ray detector along a first path, and said second spectroscopic unit is placed between the test sample and said single X-ray detector on a second path different from said first path, and is arranged and configured to guide the scattered X rays from the test sample to said X-ray detector along said second path.

5. The combination according to claim 4, further comprising:

a first slit arranged between the test sample and said first spectroscopic unit on said first path, to collect and guide the fluorescence X rays from the test sample to said first spectroscopic unit with a first angle, and a second slit arranged between the test sample and said second spectroscopic unit on said second path, to collect and guide the scattered X rays from the test sample to said second spectroscopic unit with a second angle.

6. The combination according to claim 1, wherein said first spectroscopic unit comprises a first analyzing crystal, said second spectroscopic unit comprises a second analyzing crystal, said first analyzing crystal is selected so that a relation between a first wavelength characteristic of the trace element in the test sample and a first lattice spacing of a first crystal material of the first analyzing crystal satisfies Bragg diffraction conditions, and said first curved surface is shaped so as to be tangent to a first Rowland circle, said second analyzing crystal is selected so that a relation between a second wavelength characteristic of the target of said X-ray source and a second lattice spacing of a second crystal material of the second analyzing crystal satisfies Bragg diffraction conditions, and said second curved surface is shaped so as to be tangent to a second Rowland circle, and said X-ray detector is placed at an intersection of said first Rowland circle and said second Rowland circle.

7. The combination according to claim 1, wherein said X-ray detector is a semiconductor X-ray detector having energy resolution, and said semiconductor X-ray detector is configured and adapted to detect the fluorescence X rays and the scattered X rays separately.

8. The combination according to claim 1, wherein said X-ray source is placed so as to irradiate a lower surface of the test sample with said primary X rays or a monochromatic component of said primary X-rays, said first spectroscopic unit, said second spectroscopic unit, and said X-ray detector are placed below the test sample, and said X-ray detector is a semiconductor X-ray detector.

9. The combination according to claim 1, further comprising:

a monochromatizing crystal that is placed between said X-ray source and the test sample, and that monochromatizes said primary X rays from said X-ray source to produce and irradiate the test sample with a monochromatic component of said primary X rays.

10. The combination according to claim 1, wherein said computation unit includes a memory in which is stored said calibration curve represented as calibration curve data comprising examples of an intensity ratio between an intensity of the fluorescence X rays and an intensity of the scattered X rays respectively for each one of a plurality of prior known samples having a plurality of different known contents of the trace element, a ratio calculating unit that is configured and adapted to determine said intensity ratio between the first intensity of the fluorescence X rays and the second intensity of the scattered X rays of the test sample having an unknown content of the trace element, from the detection data provided by said single X-ray detector, and a content calculating unit that is configured and adapted to calculate the content of the trace element contained in the test sample by referencing said intensity ratio determined for the test sample to the calibration curve data stored in said memory.

11. The combination according claim 1, wherein the trace element is sulfur and the test sample comprises an oil that contains the trace element.

12. An X-ray fluorescence analysis method for analyzing a trace element contained in a test sample to be analyzed, comprising:

arranging an X-ray source having a target that emits primary X rays to irradiate the test sample;

with a first spectroscopic unit having a first curved surface, selectively receiving and dispersing fluorescence X rays of the trace element that are emitted from the test sample;

with a second spectroscopic unit having a second curved surface, selectively receiving and dispersing scattered X rays that are scattered from the test sample, wherein the scattered X rays are dependent on the target of the X-ray source and are not dependent on the trace element contained in the test sample;

with a single X-ray detector, receiving the fluorescence X rays dispersed by said first spectroscopic unit and receiving the scattered X rays dispersed by said second spectroscopic unit, and detecting the fluorescence X rays and the scattered X rays; and performing a computation step of determining, from detection data provided by said single X-ray detector, an intensity ratio between a first intensity of the fluorescence X rays and a second intensity of the scattered X rays detected by the single X-ray detector, and determining a content of the trace element contained in the test sample based on the intensity ratio and a calibration curve;

wherein the trace element contained in the test sample is a light element, and wherein said X-ray source, said single X-ray detector, said first spectroscopic unit and said second spectroscopic unit are respectively selected, configured and arranged so that said computation step is able to determine the content of the trace element being a light element contained in the test sample.

13. The X-ray fluorescence analysis method according to claim 12, wherein the computation step includes
 a first step of obtaining calibration curve data representing said calibration curve as examples of an intensity ratio between an intensity of the fluorescence X rays and an intensity of the scattered X rays respectively for each one of a plurality of prior known samples having a plurality of different known contents of the trace element,
 a second step of determining the intensity ratio between the first intensity of the fluorescence X rays and the second intensity of the scattered X rays of the test sample having an unknown content of the trace element, from the detection data provided by the single X-ray detector, and
 a third step of determining the content of the trace element contained in the test sample by referencing the intensity ratio determined for the test sample to the calibration curve data.

14. A combination comprising a test sample to be analyzed and an apparatus for measuring a trace element contained in the test sample, wherein said apparatus comprises:
 an X-ray source arrangement that comprises an X-ray emission target material, and that is configured and arranged to emit X rays comprising source X rays which are characteristic of said target material, such that the source X rays impinge on the test sample, whereupon the test sample partially scatters the source X rays as scattered X rays from the test sample, and the source X rays partially cause fluorescent emission, from the test sample, of fluorescence X rays characteristic of the trace element;
 a single X-ray detector that is sensitive to detect both the scattered X rays and the fluorescence X rays;
 a first spectroscopic unit comprising a first spectroscopic element, wherein said first spectroscopic element comprises a first material selected so that, and said first spectroscopic unit is configured and arranged so that, said first spectroscopic unit selectively receives and re-directs the fluorescence X rays from the test sample to said single X-ray detector whereupon the fluorescence X rays are detected by said single X-ray detector; and
 a second spectroscopic unit comprising a second spectroscopic element, wherein said second spectroscopic element comprises a second material selected so that, and said second spectroscopic unit is configured and arranged so that, said second spectroscopic unit selectively receives and re-directs the scattered X rays from the test sample to said single X-ray detector whereupon the scattered X rays are detected by said single X-ray detector;
 wherein the trace element contained in the test sample is a light element, and wherein said X-ray source arrangement, said single X-ray detector, said first spectroscopic unit and said second spectroscopic unit are respectively selected, configured and arranged so that said apparatus is able to determine the content of the trace element being a light element contained in the test sample.

15. The combination according to claim 14, wherein said X-ray source arrangement further comprises a monochromatizing crystal interposed on a beam path between said target material and the test sample.

16. The combination according to claim 14, wherein said first spectroscopic unit further comprises a first inlet slit interposed on a beam path between the test sample and said first spectroscopic element, said second spectroscopic unit further comprises a second inlet slit interposed on a beam path between the test sample and said second spectroscopic element, and said apparatus further comprises an anti-scattering plate with a through-hole interposed on a beam path between said first spectroscopic element and said X-ray detector and on a beam path between said second spectroscopic element and said X-ray detector.

17. The combination according to claim 14,
 wherein the apparatus further comprises an analyzer device that comprises at least one computer processor and at least one memory device connected to said at least one computer processor,
 wherein said at least one memory device stores calibration curve data of a relation between known intensity ratios and known trace element contents of the trace element respectively in prior known samples having a plurality of different known trace element contents of the trace element,
 wherein the known intensity ratios are ratios of an intensity of fluorescence X rays relative to scattered X rays of the prior known samples, and
 wherein said at least one memory device further stores a program of instructions that, when executed by said at least one computer processor, calculates a test sample intensity ratio of an intensity of the fluorescence X rays of the test sample detected by said X-ray detector relative to an intensity of the scattered X rays of the test sample detected by said X-ray detector, and determines a content of the trace element in the test sample based on said test sample intensity ratio referenced to said calibration curve data.

18. The combination according to claim 17, wherein said calibration curve data is a linear function of the known intensity ratios and the known trace element contents of the trace element in the prior known samples, and said linear function is stored as said calibration curve data in said at least one memory device.

19. The combination according to claim 17, wherein said calibration curve data is a calibration curve table of data points respectively representing the known intensity ratios and the known trace element contents of the trace element in the prior known samples, and said calibration curve table is stored as said calibration curve data in said at least one memory device.

20. The combination according to claim 1, wherein said calibration curve is a linear function of intensity ratios between an intensity of fluorescence X rays and an intensity of scattered X rays respectively for each one of plural prior known samples having plural different known contents of the trace element registered in advance.

21. The combination according to claim 1, wherein said calibration curve is a calibration curve table storing data representing intensity ratios between an intensity of the fluorescence X rays and an intensity of the scattered X rays respectively for each one of plural prior known samples having plural different known contents of the trace element registered in advance.

22. The combination according to claim 1, wherein the apparatus is configured and arranged to be able to measure the content of the trace element below 0.5 ppm.

* * * * *